United States Patent

Dahl et al.

[11] Patent Number: 5,306,278
[45] Date of Patent: Apr. 26, 1994

[54] CORTICOTOMY DRILL GUIDE

[75] Inventors: Mark T. Dahl, Eagan, Minn.; Richard H. Clewett, Los Angeles, Calif.

[73] Assignee: Ace Medical Company, Los Angeles, Calif.

[21] Appl. No.: 944,211

[22] Filed: Sep. 11, 1992

[51] Int. Cl.$^5$ .................................. A61F 5/04
[52] U.S. Cl. ............................ 606/96; 408/241 G
[58] Field of Search ............... 606/96, 97, 98, 75, 606/80, 87, 88, 89, 103, 104, 130; 408/241 G

[56] References Cited

U.S. PATENT DOCUMENTS

| | | | |
|---|---|---|---|
| 2,181,746 | 11/1939 | Siebrandt | 606/96 |
| 4,421,112 | 12/1983 | Mains et al. | 606/96 |
| 4,444,180 | 4/1984 | Schneider et al. | 606/96 |
| 4,788,970 | 12/1988 | Kara et al. | 606/96 |
| 4,881,534 | 12/1989 | Uhl et al. | 606/84 |
| 4,920,958 | 5/1990 | Walt et al. | 606/96 |
| 5,078,719 | 1/1992 | Schreiber | 606/87 |
| 5,180,388 | 1/1993 | DiCarlo | 623/16 |

OTHER PUBLICATIONS

John Lindquist, "Surgical Instruments and Apparatus" *International Abstracts of Surgery*, vol. 77, p. 529 (1944).

*Primary Examiner*—Stephen C. Pellegrino
*Assistant Examiner*—Guy V. Tucker
*Attorney, Agent, or Firm*—Kinney & Lange

[57] ABSTRACT

A drill guide for use in corticotomy procedures includes a head having a first end forming tines for penetrating and gripping the bone, a second end generally opposite the first end, and a plurality of drill guide passages extending between the first and second ends. The drill guide passages are arranged at different angles to permit a drill bit to bore into the cortex at different angles and different depths to form a circumferential region of weakened cortex. In use, the drill guide is positioned on the bone at a selected fracture site and a drill bit is operated through selected guide passages to bore into the cortex at the fracture site, thereby weakening a circumferential region of the cortex. Any remaining cortex is broken to complete the corticotomy procedure.

8 Claims, 1 Drawing Sheet

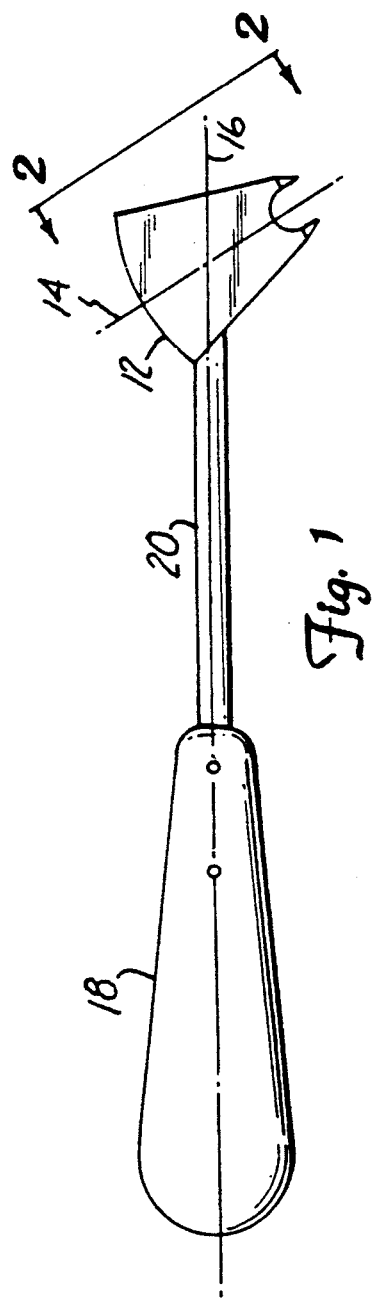
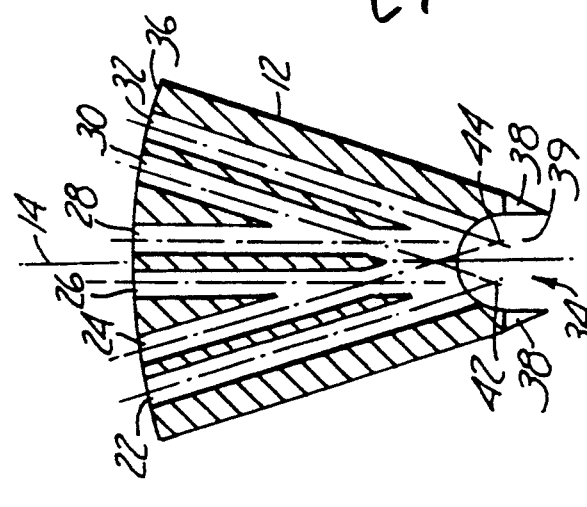
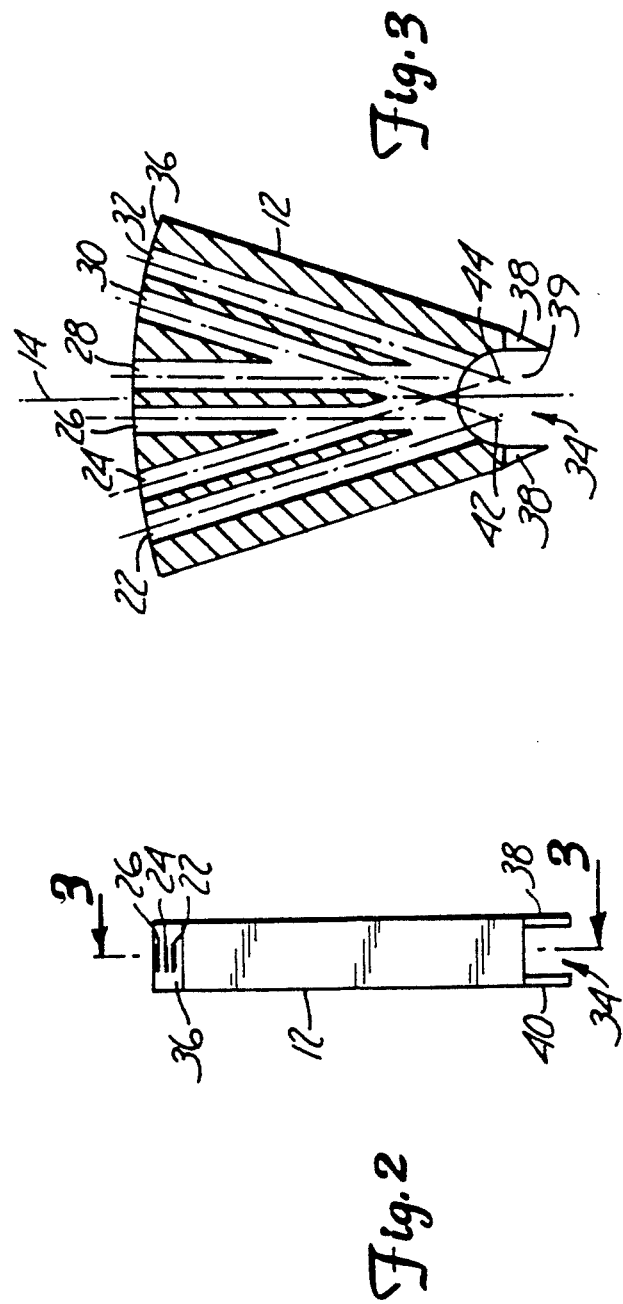

CORTICOTOMY DRILL GUIDE

BACKGROUND OF THE INVENTION

This invention relates to drill guides for use in corticotomy procedures to guide a drill bit into the cortex of a bone.

Since the early 1950s, there has existed a procedure for effective limb lengthening which involves circumferential severance of the cortex of the bone to be lengthened and gradual separation of the separated cortex ends as new bone is generated in the distraction gap. An important step to the procedure is the performance of the corticotomy procedure wherein the cortex is circumferentially severed. It is important to the corticotomy procedure that damage to the endosteum and the periosteum be minimized. These membranes are important to the regeneration of the cortex, and hence to the bone lengthening or transporting process.

Heretofore, corticotomy procedures have been performed through the use of osteotomes, power saws, and drills. Using an osteotome, the corticotomy is performed by making an incision through the periosteum and inserting a periosteal elevator medially and laterally to elevate the periosteum. An osteotome is inserted into the rent in the periosteum to cut a groove in the cortex. Care is normally taken by the surgeon not to penetrate the medullary cavity or the endosteum membrane surrounding it. Employing the osteotome, the surgeon is able to make a circumferential severance of the cortex. This procedure is explained in U.S. Pat. No. 4,881,534 issued to Uhl et al. on Nov. 21, 1989.

Reciprocating or oscillating power saws and power osteotomes have also been employed in corticotomy procedures following substantially the same procedure as described above. The principal advantage of such power devices is that they require less effort by the surgeon. However, power devices tend to slip, causing injury to the periosteum or endosteum. An example of a power device is found in the Warfield et al. U.S. Pat. No. 3,678,934 issued Jul. 25, 1972.

Manual and power drills have also been used to bore into the cortex to form a circumferential region of weakened cortex which may be broken and removed. By carefully and repeatedly boring the drill into the cortex at different angles and different depths, a circumferential severance of the cortex may be accomplished. However, a difficulty with drilling is that there has been no effective means for guiding the drill bit to accurately locate the drill position for the different angles and to reduce likelihood of damage to the periosteum and endosteum.

SUMMARY OF THE INVENTION

The present invention is directed to a drill guide for use in corticotomy procedures. The drill guide includes a head having a first end forming tines for gripping the bone, a second end generally opposite the first end, and a plurality of guide passages extending between the first and second ends. The guide passages are sized to receive a drill bit, and are disposed at different angles with respect to each other as to converge at different angles at the first end.

Conveniently, a handle is connected to the head and disposed at a different angle to each of the guide passages, the handle being arranged to permit the surgeon to manipulate the head.

Also conveniently, the guide passages converge at an opening at the first end of the head as to form teeth on opposite sides of the opening to grip the bone.

In the use of the drill guide according to the present invention, a fracture site is selected from where cortex is to removed. The drill guide is positioned on the bone at the fracture site. A drill bit is operated through selected guide passages to bore into the cortex at the fracture site, thereby weakening a circumferential region of the cortex. Cortex remaining from the boring procedure is broken to complete the corticotomy procedure.

Advantageously, the procedure is accomplished after opening the periosteum and the drill guide is gripped to the cortex to be removed.

BRIEF DESCRIPTION OF THE DRAWINGS

FIG. 1 is a side view of a drill guide in accordance with the presently preferred embodiment of the present invention.

FIG. 2 is an end view of the head of the drill guide taken from along a line 2—2 in FIG. 1.

FIG. 3 is a section view taken alone line 3—3 in FIG. 2.

DETAILED DESCRIPTION OF THE PREFERRED EMBODIMENTS

FIG. 1 illustrates a drill guide 10 in accordance with the presently preferred embodiment of the present invention. Guide 10 includes a head 12 having a nominal axis 14 disposed at an acute angle to axis 16 of handle 18. Conveniently, handle 18 is axially mounted to shaft 20, which is integral to head 12.

As shown particularly in FIG. 3, head 12 is essentially a pie-shaped head having a plurality of guide passages 22, 24, 26, 28, 30 and 32 extending from a first end shown generally at 34 to a second end surface 36 of head 12. A pair of opposing tines or teeth 38 are formed on one side of head 12 and a pair of opposing tines or teeth 40 are formed on the opposite side of head 12 at the end 34. Teeth 38 and 40 are spaced apart at end 34 to permit passage therebetween of a drill bit extending from a passage 22-32. Passages 22-32 converge at end 34 to form an opening 39 between teeth 38 and 40.

As shown particularly in FIG. 3, the axes of a first group of guide passages 22, 26 and 30 are arranged to converge at point 42 in open region 39 slightly off center from axis 14 of the head. Likewise, the axes of a second group of guide passages 24, 28 and 32 are arranged to converge at point 44 in open region 39 offset from axis 14 oppositely from point 42. Moreover, the axes of passages 26 and 28 are parallel to axis 14, the axes of passages 22 and 24 are parallel to each other and at an angle to axis 14, and the axes of passages 30 and 32 are parallel to each other and also at an angle to axis 14. Axis 14 and the axes of guide passages 22, 24, 26, 28, 30 and 32 are coplanar in the single plane of FIG. 3. Conveniently, the angle between axis 14 and the axes of passages 22 and 24 may be equal to and opposite the angle between axis 14 and axes 30 and 32. An angle of about 17° is preferred. Each of guide passages 22, 24, 26, 28, 30 and 32 has the same diameter, such as about 0.122 inches, to accept a drill bit of about 3.0 mm.

Teeth 38 and 40 are preferably sharp teeth to penetrate and grip the cortex of the bone. The opposing edges of the teeth are parallel to axis 14 and the outside edges of the teeth being approximately 25° from axis 14.

In the use of the drill guide in accordance with the present invention, end 34 of the drill guide is positioned against the bone so that teeth 38 and 40 grip the bone and/or cortex. To aid in the gripping action, a mallet or other impact driving instrument may be applied to surface 36 of the drill guide so that teeth 38 and 40 penetrate into the bone and cortex to grip the bone. Thus, surface 36 is curved to accept a driving force, and head 12 is constructed of durable stainless steel to withstand the impact force. A drill bit is inserted into a selected guide passage 22-32 and operated to bore into the cortex of the bone. When the desired depth is reached, preferably as to not penetrate the medullary cavity or damage the periosteum, the drill bit is withdrawn and inserted into another selected guide passage of the drill guide and the procedure is repeated. It may be desired in some cases to bore through the endosteum and medullary cavity to reach cortex at the opposite side of the medullary cavity.

It may be convenient to bore the cortex along one side of the medullary cavity at a first position of the drill guide and then reposition the drill guide and repeat the procedure for the opposite side of the medullary cavity. In any case, multiple holes are bored into the cortex in the region surrounding the medullary cavity. Remaining cortex is weakened by the multiple bores and is removed from the circumferential groove by breaking and removing, such as with an osteotome.

Advantageously, the periosteum may be cut and a periosteal elevator inserted to elevate the periosteum before positioning the drill guide. The drill guide is thus inserted into the rent in the periosteum to grip the cortex. Employing this initial step subjects the periosteum to less injury, thereby facilitating regeneration of the cortex.

Although the present invention has been described with reference to preferred embodiments, workers skilled in the art will recognize that changes may be made in form and detail without departing from the spirit and scope of the invention.

What is claimed is:

1. A drill guide for use in corticotomy procedures to guide a drill bit into the cortex of a bone, the drill guide comprising a head having:
   (a) a first end having tines for gripping the bone;
   (b) a second end generally opposite the first end;
   (c) a nominal axis extending through the first and second ends; and
   (d) a plurality of guide passages in the head extending between and open to the first and second ends, the guide passages being arranged in first and second groups, each group containing a plurality of guide passages, the guide passages being sized to receive a drill bit, each guide passage of the first group having an axis arranged at an angle to the nominal axis which is different from the angle between the nominal axis and the axis of each other guide passage of the first group, the guide passage axes of the first group being arranged to converge at a point offset from the nominal axis of the head in a first direction, and each guide passage of the second group having an axis arranged at an angle to the nominal axis which is different from the angle between the nominal axis and the axis of each other guide passage of the second group, the guide passage axes of the second group being and arranged to converge at the first end at a point offset from the nominal axis of the head in a second direction opposite the first direction, the guide passage axes of both the first and second groups lying in a single plane and the axis of each guide passage of the first group being parallel to the axis of a guide passage of the second group; and a handle mounted to the head at a side of the head between the first and second ends, the handle having an axis disposed at an angle to the nominal axis of the head.

2. A drill guide according to claim 1 wherein the guide passages converge adjacent the first end of the head, the tines comprising first and second teeth positioned on opposite sides of the nominal axis of the head, the points of convergence of the first and second groups of guide passage axes being between the first and second teeth.

3. A drill guide according to claim 2 wherein the second end forms an impact surface against which the drill guide may be driven so that the teeth grip the bone.

4. A drill guide according to claim 1 wherein the second end forms an impact surface against which the drill guide may be driven so that the tines grip the bone.

5. A drill guide according to claim 1 wherein the angle between the axis of the handle and the nominal axis is acute.

6. A drill guide for use in corticotomy procedures to guide a drill bit into the cortex of a bone exposed through an opening in the periosteum of the bone, the drill guide comprising:
   (a) a head arranged to extend through the opening in the periosteum, the head having a nominal axis and including a first end having first and second teeth extending from the first end and arranged to grip the exposed cortex, an open region at the first end and between the first and second teeth; a second end generally opposite the first end arranged to be exterior of the periosteum when the teeth grip the cortex; and a plurality of guide passages extending between the first and second ends, each guide passage having an axis, the guide passages being arranged in first and second groups, each group containing a plurality of guide passages, each guide passage of the first group having an axis arranged at an angle to the nominal axis which is different from the angle between the nominal axis and the axis of each other guide passage of the first group, the guide passage axes of the first group being arranged to converge at a first point in the open region between the first and second teeth offset from the nominal axis of the head in a first direction, and each guide passage of the second group having an axis arranged at an angle to the nominal axis which is different from the angle between the nominal axis and the axis of each other guide passage of the second group, the guide passage axes of the second group being arranged to converge at a second point in the open region between the first and second teeth offset from the nominal axis of the head in a second direction opposite the first direction, the guide passages being sized to receive a drill bit, the guide passage axes of both the first and second groups lying in a single plane and the axis of each guide passage of the first group being parallel to the axis of a guide passage of the second group; and
   (b) a handle mounted to the head at a location on the head exteriorly of the bone when the teeth grip the cortex.

7. A drill guide according to claim 6 wherein the second end forms an impact surface against which the drill guide may be driven so that the teeth grip the bone.

8. A method of performing a corticotomy comprising: selecting a fracture site where the cortex is to be removed;

cutting through and opening the periosteum to expose the cortex at the fracture site;

positioning a drill guide on the exposed cortex at the fracture site, the drill guide having a head having a nominal axis, a first end having first and second tines for gripping the cortex, a second end generally opposite the first end arranged to be exterior of the bone when the tines grip the cortex, and first and second groups of guide passages extending between the first and second ends, each group containing a plurality of guide passages, each guide passage of the first group having an axis arranged at an angle to the nominal axis which is different from the angle between the nominal axis and the axis of each of the other guide passages of the first group, the guide passage axes of the first group being arranged to converge at a first point in an open region formed at the first end between the first and second tines, the first point being offset from the nominal axis of the head in a first direction, and each guide passage of the second group having an axis arranged at an angle to the nominal axis which is different from the angle between the nominal axis and the axis of each of the other guide passages of the second group, the guide passage axes of the second group being arranged to converge at a second point in the open region between the first and second tines, the second point being offset from the nominal axis of the head in a second direction opposite the first direction, the guide passage axes of both the first and second groups lying in a single plane and the axis of each guide passage of the first group being parallel to the axis of a guide passage of the second group, the guide passages being sized to receive a drill bit;

operating the drill guide so that the tines grip the cortex;

operating a drill bit through selected ones of the guide passages to remove cortex from the bone at the fracture site to weaken the cortex; and breaking the cortex remaining between the regions from which cortex had been removed.

* * * * *

UNITED STATES PATENT AND TRADEMARK OFFICE
CERTIFICATE OF CORRECTION

PATENT NO. : 5,306,278

DATED : April 26, 1994

INVENTOR(S) : MARK T. DAHL, RICHARD H. CLEWETT

It is certified that error appears in the above-identified patent and that said Letters Patent is hereby corrected as shown below:

Col. 2, line 6, after "is to", insert --be--

Signed and Sealed this

Second Day of August, 1994

Attest:

BRUCE LEHMAN

Attesting Officer

Commissioner of Patents and Trademarks